United States Patent
Kashiwazaki

(10) Patent No.: US 9,974,517 B2
(45) Date of Patent: May 22, 2018

(54) ULTRASOUND ENDOSCOPE

(71) Applicant: OLYMPUS CORPORATION, Tokyo (JP)

(72) Inventor: Yosuke Kashiwazaki, Kodaira (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days. days.

(21) Appl. No.: 15/427,453

(22) Filed: Feb. 8, 2017

(65) Prior Publication Data
US 2017/0143299 A1 May 25, 2017

Related U.S. Application Data

(63) Continuation of application No. PCT/JP2015/075326, filed on Sep. 7, 2015.

(30) Foreign Application Priority Data

Sep. 12, 2014 (JP) .................................. 2014-186741

(51) Int. Cl.
A61B 8/14 (2006.01)
A61B 8/12 (2006.01)
A61B 1/005 (2006.01)
A61B 1/015 (2006.01)
A61B 1/06 (2006.01)

(52) U.S. Cl.
CPC .............. A61B 8/12 (2013.01); A61B 1/0051 (2013.01); A61B 1/015 (2013.01); A61B 1/0669 (2013.01)

(58) Field of Classification Search
CPC .. A61B 1/00; A61B 8/12; H01L 23/50; H01R 13/66; H01R 24/20
See application file for complete search history.

(56) References Cited

U.S. PATENT DOCUMENTS

2004/0143162 A1* 7/2004 Krattiger ............ A61B 1/00096
600/175

FOREIGN PATENT DOCUMENTS

JP 2002-143166 A 5/2002
JP 2009-240658 A 10/2009
JP 5572781 B1 8/2014

OTHER PUBLICATIONS

International Search Report dated Dec. 1, 2015 issued in PCT/JP2015/075326.

* cited by examiner

Primary Examiner — Mark Remaly
(74) Attorney, Agent, or Firm — Scully, Scott, Murphy & Presser, P.C.

(57) ABSTRACT

An ultrasound endoscope includes: an insertion portion configured to be inserted into a subject; a distal end portion provided at a distal end of the insertion portion and including at least one fitting groove; an ultrasound transducer unit configured to be attachable to and detachable from the distal end portion and including at least one projecting portion configured to be freely fitted into the fitting groove and projecting outside in a diameter direction K of the distal end portion; and a gap for removal of the ultrasound transducer unit, the gap being formed between the projecting portion fitted in the fitting groove and the fitting groove.

8 Claims, 7 Drawing Sheets

ULTRASOUND ENDOSCOPE

CROSS REFERENCE TO RELATED APPLICATION

This application is a continuation application of PCT/JP2015/075326 filed on Sep. 7, 2015 and claims benefit of Japanese Application No. 2014-186741 filed in Japan on Sep. 12, 2014, the entire contents of which are incorporated herein by this reference.

BACKGROUND OF THE INVENTION

1. Field of the Invention

The present invention relates to an ultrasound endoscope configured so that an ultrasound transducer unit is attachable to and detachable from a distal end portion of an insertion portion configured to be inserted into a subject.

2. Description of the Related Art

An ultrasound endoscope is well known which obtains an ultrasound image of an examination target region by transmitting ultrasound to the examination target region in a subject from an ultrasound transducer held in a housing of an ultrasound transducer unit provided on a distal end portion of an insertion portion and receiving the ultrasound from the examination target region.

Further, a configuration is well known in which the ultrasound transducer unit is attachable to and detachable from the distal end portion of the insertion portion. More specifically, a configuration is well known in which, by a proximal end side of the housing of the ultrasound transducer unit being freely fitted into an ultrasound transducer unit mounting hole (hereinafter referred to simply as a mounting hole) found in a distal end portion body constituting the distal end portion, and screws being freely screwed into screw holes formed in outer circumferences of the distal end portion body and the housing, from an outer side of the distal end portion in a diameter direction, the housing is attachable to and detachable from the mounting hole.

Here, there is a problem that, if countersunk screws having head portions are used as the screws for fixing the housing to the distal end portion body, the head portions project from an outer circumferential face of the distal end portion body after the screws are screwed in the respective screw holes, and reduction of a diameter of the distal end portion of the outer circumferential face is hindered.

In view of such a problem, Japanese Patent Application Laid-Open Publication No. 2002-143166 discloses a configuration of an ultrasound endoscope in which the head portions of the screws are prevented from projecting from the outer circumferential face of the distal end portion body by adopting counterbore holes as the screw holes in which the screws are screwed on the distal end portion body.

By the way, as disclosed in Japanese Patent Application Laid-Open Publication No. 2002-143166, when the housing is screwedly fixed relative to the mounting hole of the distal end portion body, a distal end side of the housing which has the ultrasound transducer inside projects forward more than a distal end face of the distal end portion body. Note that the housing is positioned by a proximal end of the housing being caused to come into contact with a part of the distal end portion body.

Therefore, if a diameter-increased part which protrudes outside in the diameter direction exists on an outer circumferential face on the distal end side of the housing, a circumferential gap occurs along a circumferential direction of the distal end portion, between the diameter-increased part and the distal end face of the distal end portion body due to design tolerance.

Here, the insertion portion is a part configured to be inserted into a subject as described above. Therefore, if a gap occurs on an outer surface, dirt accumulates in the gap.

When dirt accumulates, hygiene problems occur. Therefore, an operator has to remove the dirt in the gap each time he uses the endoscope, and it is very troublesome to the operator. Therefore, a configuration is well known in which the circumferential gap which has occurred on the outer surface is filled with adhesive or the like.

SUMMARY OF THE INVENTION

An ultrasound endoscope according to an aspect of the present invention includes: an insertion portion configured to be inserted into a subject; a distal end portion provided at a distal end of the insertion portion and including at least one fitting groove; an ultrasound transducer unit configured to be attachable to and detachable from the distal end portion and including at least one projecting portion configured to be freely fitted into the fitting groove and projecting outside in a diameter direction of the distal end portion; and a gap for removal of the ultrasound transducer unit, the gap being formed between the projecting portion fitted in the fitting groove and the fitting groove.

Further, an ultrasound endoscope according to another aspect of the present invention includes: an insertion portion configured to be inserted into a subject; a distal end portion provided at a distal end of the insertion portion and including at least one fitting groove; an ultrasound transducer unit configured to be attachable to and detachable from the distal end portion; at least one projecting portion formed on the ultrasound transducer unit, configured to be freely fitted into the fitting groove, and projecting outside in a diameter direction which is a direction vertical to a longitudinal axis of the insertion portion; and a fixing member configured to fix the distal end portion and the ultrasound transducer unit to each other in a state that a gap is formed between an inner circumferential face of the fitting groove and an outer circumferential face of the projecting portion fitted in the fitting groove.

DETAILED DESCRIPTION OF THE PREFERRED EMBODIMENT(S)

An embodiment of the present invention will be described below with reference to drawings. It should be noted that the drawings are schematic drawings, and a relationship between thickness and width of each member, a thickness ratio among respective members and the like are different from actual ones, and, of course, portions having a different mutual dimensional relationship or ratio may be included among the drawings.

An embodiment of the present invention will be described below with reference to drawings.

Figure 1:
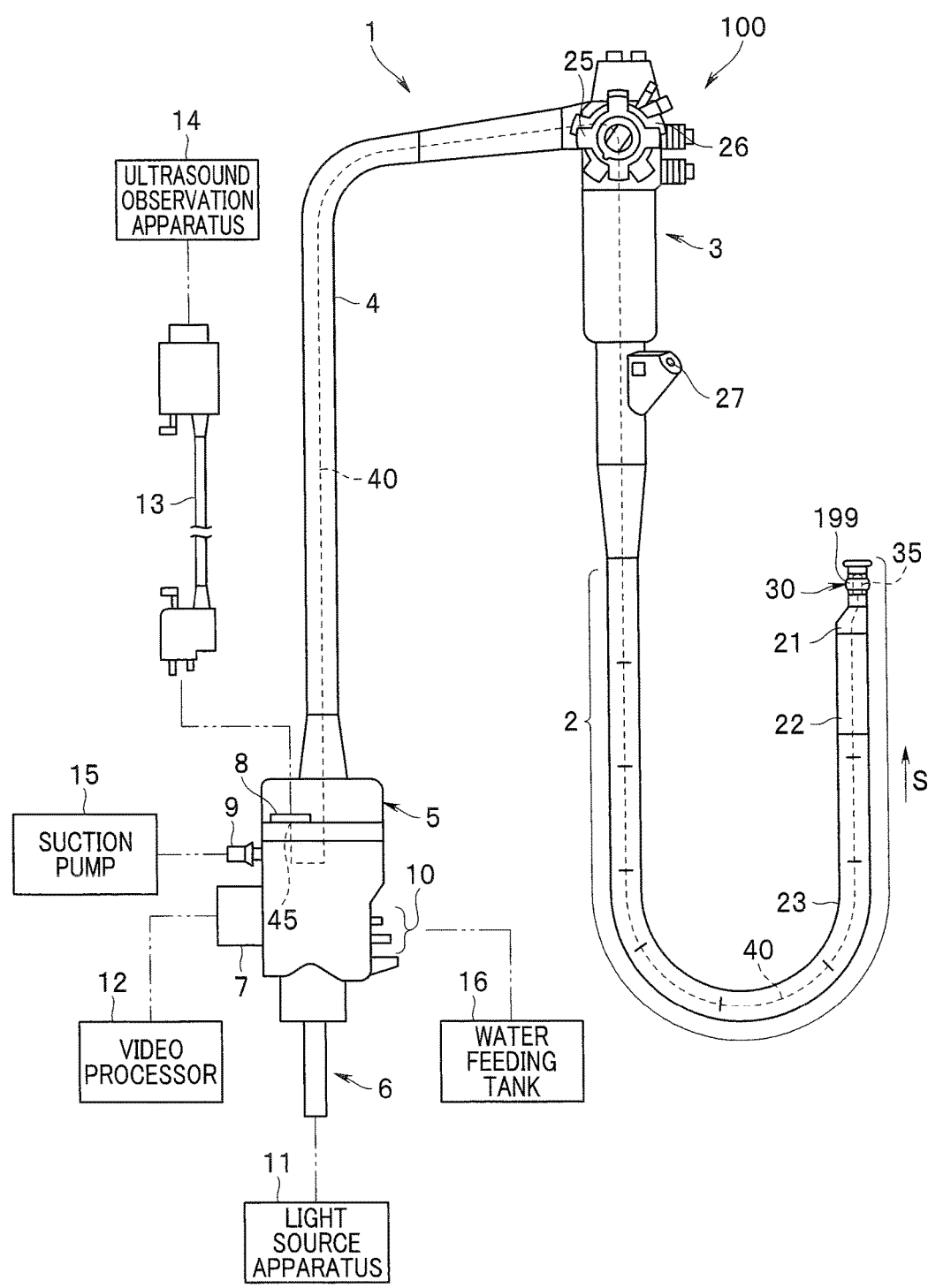
FIG. 1 is a diagram showing an ultrasound endoscope apparatus provided with an ultrasound endoscope of the present embodiment.

FIG. 1 is a diagram showing an ultrasound endoscope apparatus provided with an ultrasound endoscope of the present embodiment. As shown in FIG. 1, an ultrasound endoscope apparatus 100 is provided with an ultrasound endoscope 1, a light source apparatus 11, a video processor 12, an ultrasound observation apparatus 14, a suction pump 15 and a water feeding tank 16, which constitute main portions of the ultrasound endoscope apparatus 100.

Main portions of the ultrasound endoscope 1 are configured with an elongated insertion portion 2 configured to be inserted into a subject, an operation portion 3 provided at a proximal end of the insertion portion 2 and configured to serve as a grasping portion also, a universal cord 4 having flexibility and extended from the operation portion 3, and an endoscope connector 5 provided at an extension end of the universal cord 4.

The endoscope connector 5 is provided with a light source connector 6, an electrical connector 7, an ultrasound connector 8, a suction pipe sleeve 9 and an air/water feeding pipe sleeve 10.

A configuration is adopted in which the light source apparatus 11 configured to supply illuminating light is attachable to and detachable from the light source connector 6. Further, a configuration is adopted in which the video processor 12 configured to perform various signal processing and the like is attachable to and detachable from the electrical connector 7 via a signal cable not shown.

Furthermore, a configuration is adopted in which the ultrasound observation apparatus 14 is attachable to and detachable from the ultrasound connector 8 to which a connector 45 provided at a proximal end of an ultrasound transducer cable 40 extending from an ultrasound transducer 35 in an ultrasound transducer unit 30 to be described later is electrically connected, via an ultrasound cable 13.

Further, a configuration is adopted in which the suction pump 15 is attachable to and detachable from the suction pipe sleeve 9 via a suction tube not shown. Furthermore, a configuration is adopted in which the water feeding tank 16 is attachable to and detachable from the air/water feeding pipe sleeve 10 via an air/water feeding tube not shown.

The ultrasound observation apparatus 14 is configured to perform various operation controls of the ultrasound endoscope 1, and performs, for example, drive control of the ultrasound transducer 35 and an operation of performing signal processing of an electrical signal acquired by the drive control of the ultrasound transducer 35 to generate a video signal.

Note that the video signal generated by the ultrasound observation apparatus 14 is outputted to a display apparatus not shown. As a result, an ultrasound image is displayed on a screen of the display apparatus which has received the video signal.

The insertion portion 2 of the ultrasound endoscope 1 is configured with a distal end portion 21, a bending portion 22 configured to be bendable, for example, in an up-and-down direction and a left-and-right direction and a long flexible tube portion 23 having flexibility, which are connected along an insertion direction S in that order from a distal end side. Note that the ultrasound transducer unit 30 is attachable to and detachable from the distal end portion 21.

The operation portion 3 is provided with bending operation knobs 25 and 26 for performing a bending operation of the bending portion 22. Further, at a position on the insertion portion 2 side of the operation portion 3, a treatment instrument insertion port 27 is provided through which a treatment instrument is introduced into a subject via the insertion portion 2 and a treatment instrument insertion conduit 127 (see FIG. 2) provided in the operation portion 3, which is described later.

The video processor 12 generates a standard video signal by performing signal processing for an electrical signal transmitted from an image pickup unit 70 (see FIG. 4) provided in the distal end portion 21, which is described later, outputs the video signal to the display apparatus not shown, and causes an endoscope observation image to be displayed on the screen of the display apparatus.

Note that, by being connected to the air/water feeding pipe sleeve 10, the water feeding tank 16 supplies fluid to a fluid supply nozzle 51 (see FIG. 2) via an air/water feeding conduit provided in the ultrasound endoscope 1, which is not shown, and supplies fluid to a balloon 199 provided on the ultrasound transducer unit 30 via a balloon conduit 19 (see FIG. 2) provided in the ultrasound endoscope 1, which is described later.

Note that the balloon conduit 19 branches from the air/water feeding conduit in the operation portion 3, and fluid supply to the fluid supply nozzle 51 and fluid supply to the balloon 199 are switched, for example, by different amounts of pressing of an air/water feeding button provided on the operation portion 3, which is not shown.

Further, gas supply and liquid supply to the fluid supply nozzle 51 are switched, for example, by whether a hole formed in the air/water feeding button, which is not shown, is closed or not.

Furthermore, because of being connected to the suction pipe sleeve 9, the suction pump 15 sucks humor and the like in a subject via the treatment instrument insertion conduit 127 provided in the ultrasound endoscope 1, which is described later, and sucks fluid from the balloon 199 via a balloon conduit 19.

Note that suction using the treatment instrument insertion conduit 127 and suction using the balloon conduit 19 are switched, for example, by different amounts of pressing of a suction button provided on the operation portion 3, which is not shown.

Next, a configuration for attaching and detaching the ultrasound transducer unit 30 to and from the distal end portion 21 will be described with use of FIGS. 2 to 8.

Figure 2:
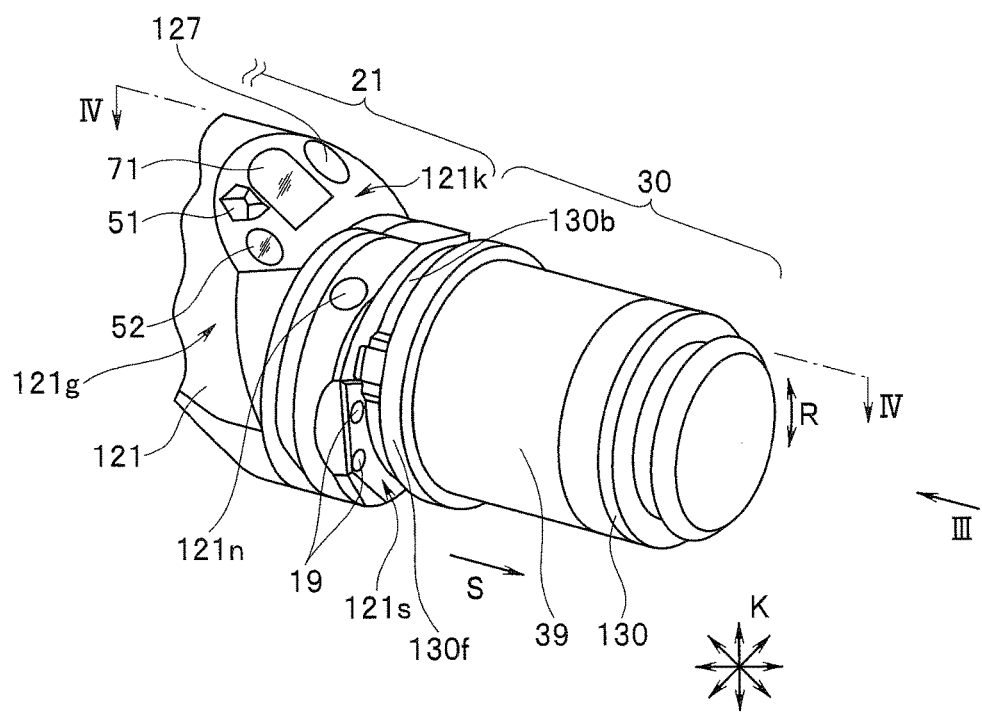
FIG. 2 is a partial perspective view showing a distal end side of an insertion portion of the ultrasound endoscope of FIG. 1.
Figure 3:
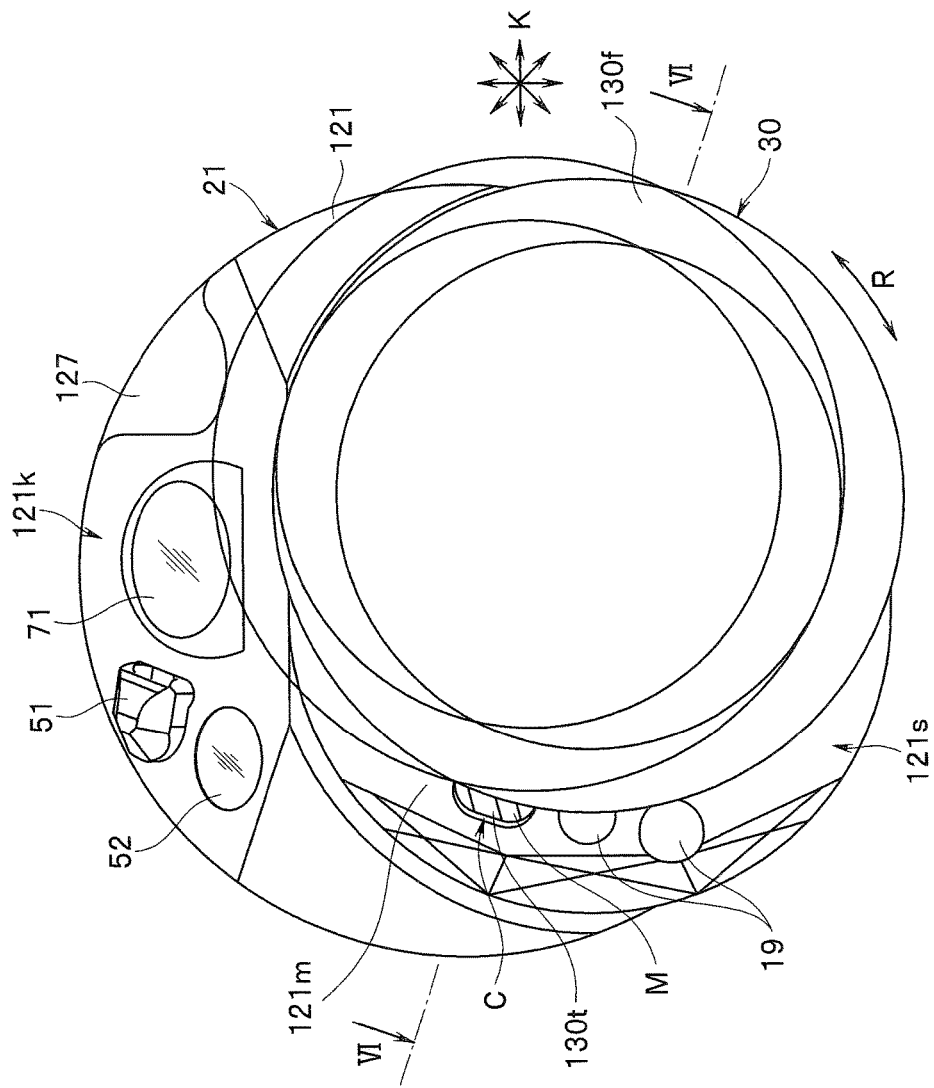
FIG. 3 is a front view of the distal end side of the insertion portion of FIG. 2 when seen from a III direction in FIG. 2.
Figure 4:
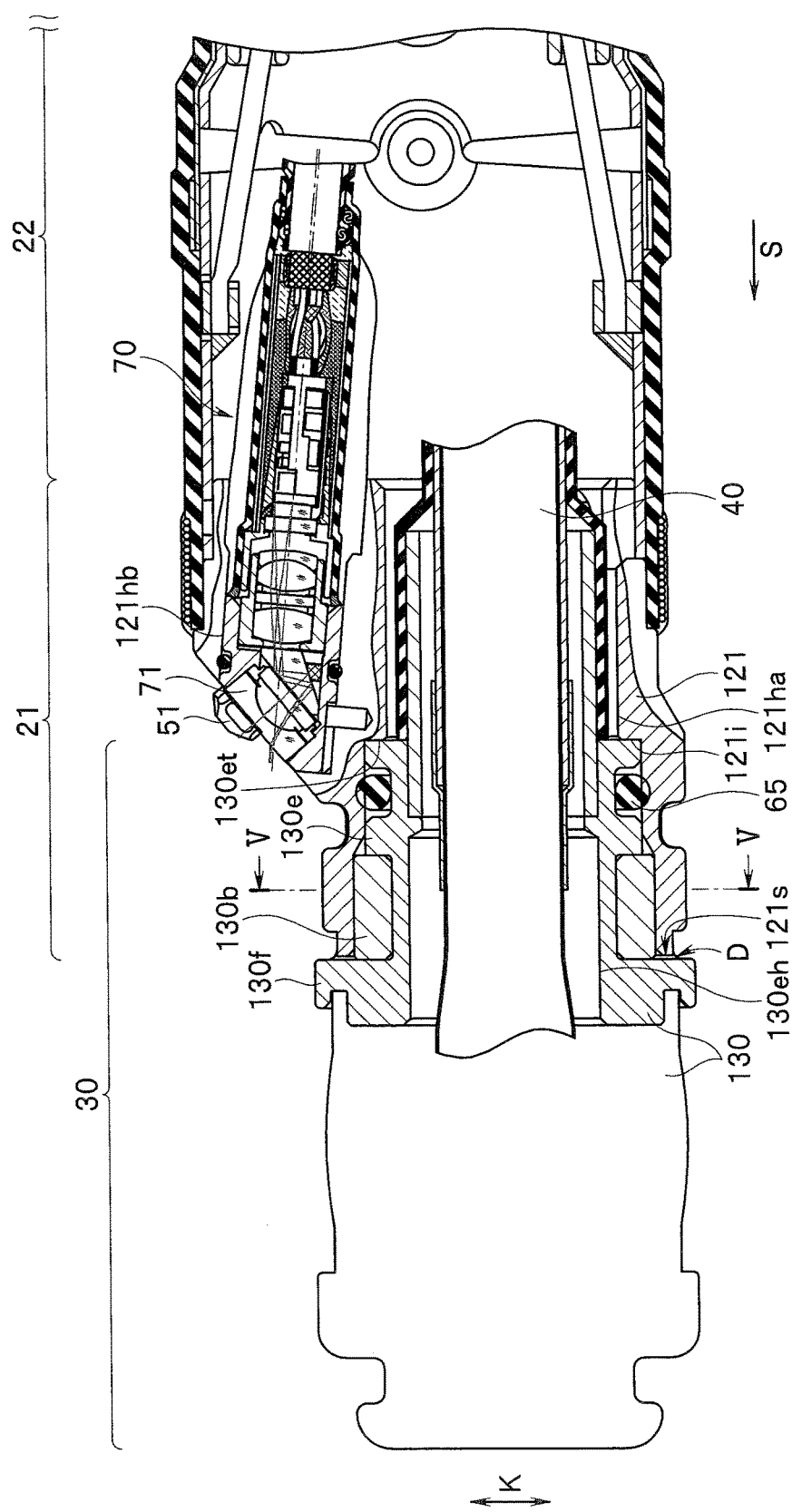
FIG. 4 is a partial cross-sectional view of the distal end side of the insertion portion along a IV-IV line in FIG. 2.
Figure 5:
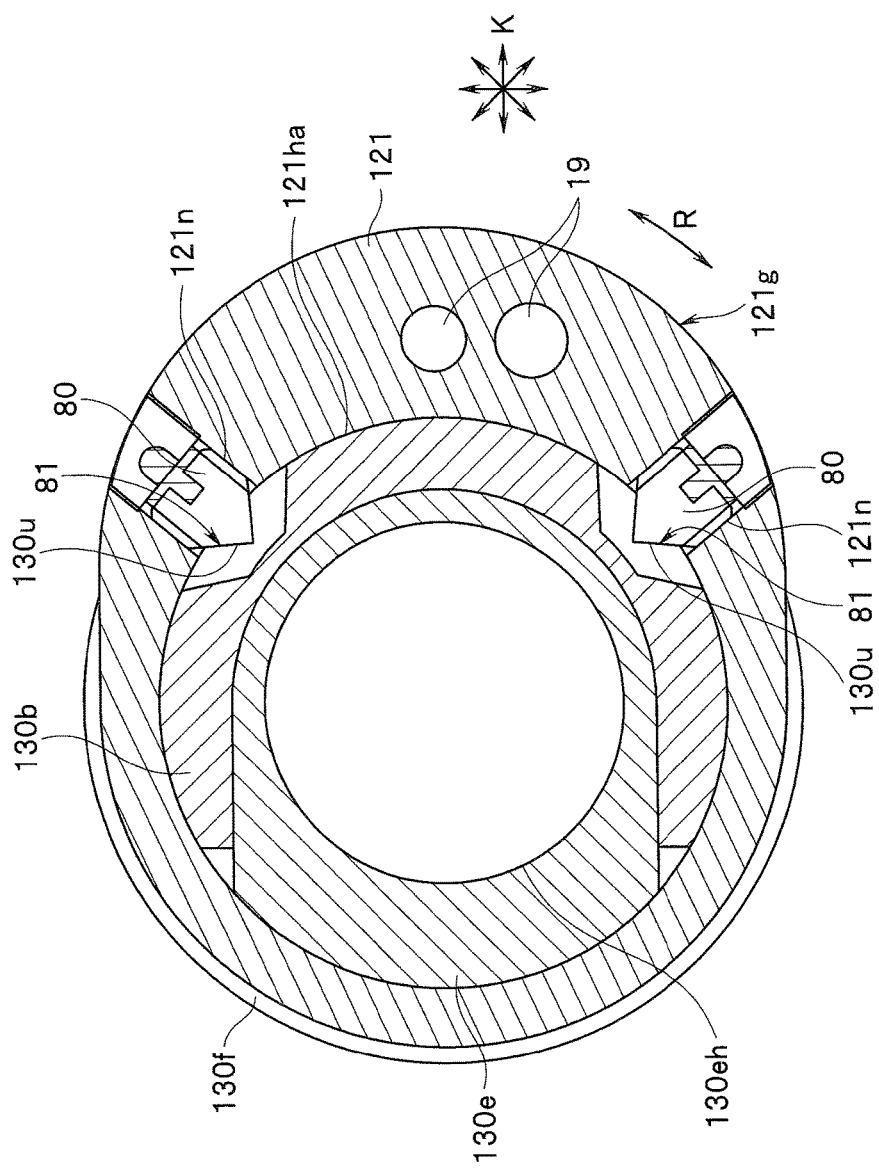
FIG. 5 is a cross-sectional view of the distal end side of the insertion portion along a V-V line in FIG. 4.

FIG. 2 is a partial perspective view showing the distal end side of the insertion portion of the ultrasound endoscope of FIG. 1; FIG. 3 is a front view of the distal end side of the insertion portion of FIG. 2 when seen from a III direction in FIG. 2; FIG. 4 is a partial cross-sectional view of the distal end side of the insertion portion along a IV-IV line in FIG. 2; FIG. 5 is a cross-sectional view of the distal end side of the insertion portion along a V-V line in FIG. 4; and FIG. 6 is a partial cross-sectional view of the distal end side of the insertion portion along a VI-VI line in FIG. 3.

Figure 6:
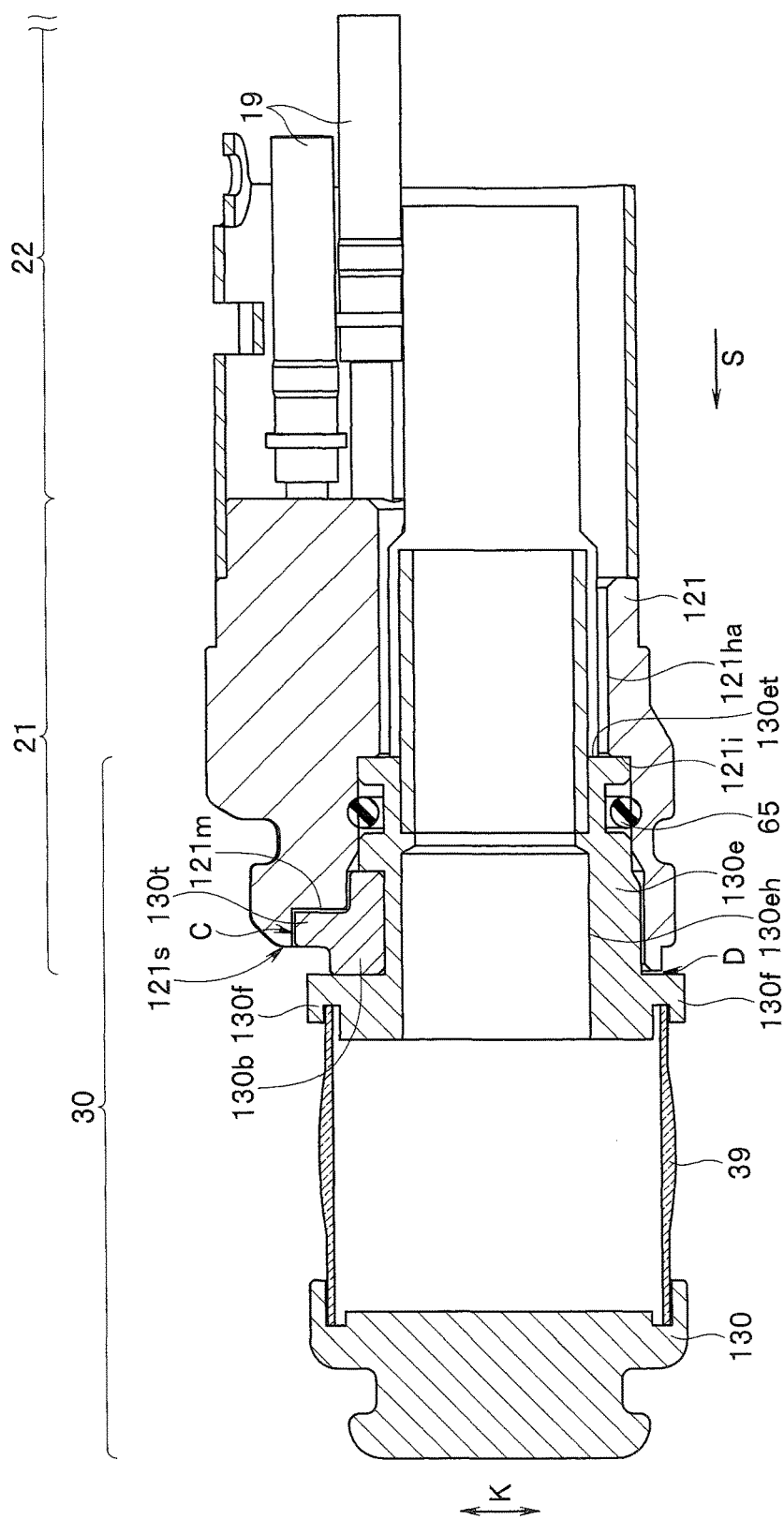
FIG. 6 is a partial cross-sectional view of the distal end side of the insertion portion along a VI-VI line in FIG. 3.
Figure 7:
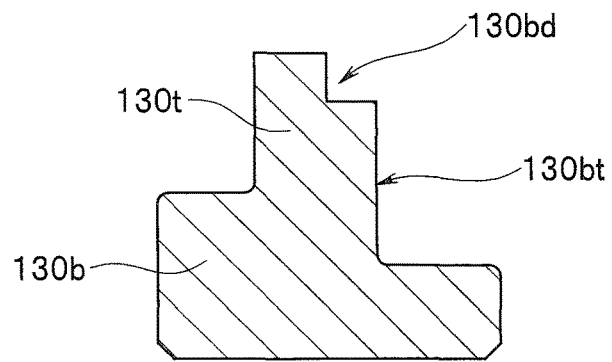
FIG. 7 is a cross-sectional view showing a modification in which a step portion is provided on a part of a face which comes in contact with a fitting groove of a projecting portion in FIG. 6.
Figure 8:
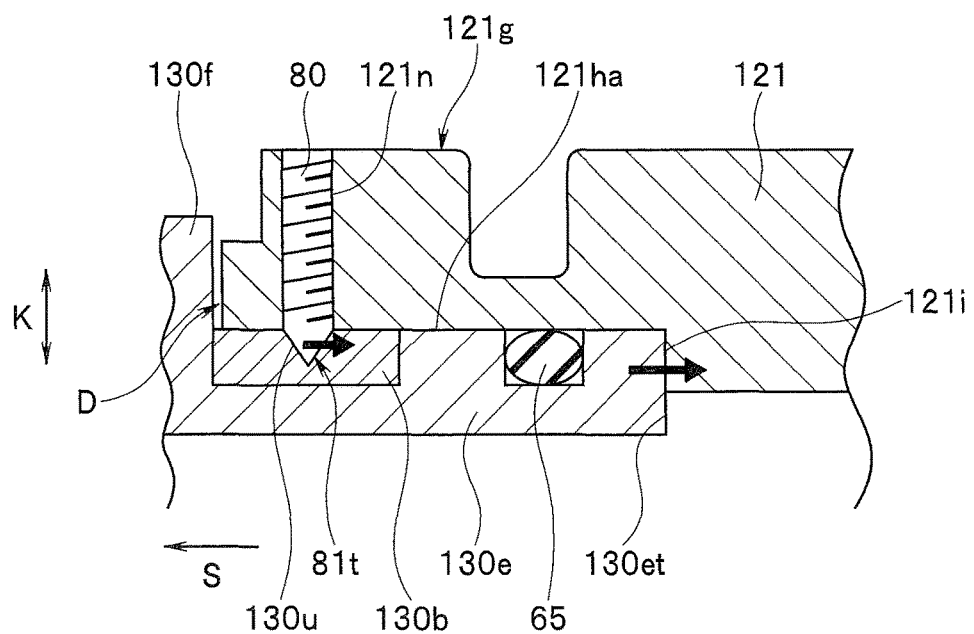
FIG. 8 is a partial cross-sectional view showing a state that a proximal end of a housing of an ultrasound transducer unit is pressed to an abutting face of a distal end portion body of a distal end portion by fully threaded screws in FIG. 5, and the housing is fixed to a mounting hole of the distal end portion body.

FIG. 7 is a cross-sectional view showing a modification in which a step portion is provided on a part of a face which comes in contact with a fitting groove of a projecting portion in FIG. 6; and FIG. 8 is a partial cross-sectional view showing a state that a proximal end of a housing of the ultrasound transducer unit is pressed to an abutting face of a distal end portion body of the distal end portion by fully threaded screws 80 in FIG. 5, and the housing is fixed to mounting holes 121ha and 121hb of the distal end portion body.

As shown in FIG. 4, the distal end portion 21 is provided with the distal end portion body 121 having a substantially cylindrical shape. In the distal end portion body 121, each of the mounting holes 121ha and 121hb passing through the distal end portion body 121 along the insertion direction S is formed.

A distal end side of the image pickup unit 70 is fixed in the mounting hole 121hb with screws not shown.

Further, as shown in FIGS. 2 to 4, the distal end portion body 121 has a notch face 121k pointing forward in the insertion direction S (hereinafter referred to simply as forward), which is obtained by cutting off a part of an outer circumferential face 121g on a distal end side. An objective lens 71 constituting the image pickup unit 70 is exposed on the notch face 121k.

Note that, in addition to the objective lens 71, a distal end opening of the treatment instrument insertion conduit 127, an illumination lens 52 configured to supply illuminating light into a subject, the fluid supply nozzle 51 configured to supply fluid to the objective lens 71, and the like are provided on the notch face 121k as shown in FIGS. 2 and 3.

Further, as shown in FIGS. 2 and 3, distal ends of the two balloon conduits 19 are opened on a distal end face 121s of the distal end portion body 121. One of the two balloon conduits 19 constitutes a fluid supply conduit configured to supply fluid with good acoustic transmissibility to the balloon 199, and the other constitutes a fluid suction conduit configured to suck fluid with good acoustic transmissibility from the balloon 199.

Furthermore, as shown in FIG. 3, a fitting groove 121m into which the projecting portion 130t of the ultrasound transducer unit 30, which is described later, is to be fitted is formed near each distal end opening of the two balloon conduits 19 in a circumferential direction R on the distal end face 121s.

Note that, as for the fitting groove 121m, a plurality of fitting grooves 121m may be formed on the distal end face 121s. Further, the fitting groove 121m may be formed on a part other than the distal end face 121s on the distal end portion body 121.

Furthermore, as shown in FIGS. 2, 5 and 8, for example, two female screw portions 121n passing through the outer circumferential face 121g and the mounting hole 121ha along a diameter direction K are formed on an outer circumference of the distal end portion body 121, at positions more frontward than the notch face 121k and more backward in the insertion direction S (hereinafter referred to simply as backward) than the distal end face 121s.

Note that the number of the female screw portions 121n is not limited to two. As shown in FIG. 8, screws having sharp tips, specifically, the known fully threaded screws 80 are screwed from outside in the diameter direction K. Note that a fully threaded screw is a screw without a head portion and with a thread formed over a whole outer circumferential face.

Further, as shown in FIGS. 4 to 6, the ultrasound transducer unit 30 is fitted and fixed in the mounting hole 121ha.

More specifically, a fitted part 130e fitted to the distal end portion 21, which is a part on a more proximal end side than a diameter-increased part 130f provided at a midway position in the insertion direction S on an outer circumference of the housing 130 of the ultrasound transducer unit 30 is fitted in the mounting hole 121ha via an O-shaped ring 65.

Note that the diameter-increased part 130f is used at time of fitting the balloon 199 on a more outer side than an acoustic lens 39 in the diameter direction K, on a more distal end side than the diameter-increased part 130f and, additionally, used to hold the acoustic lens 39. Further, as shown in FIG. 4, a diameter-increased part is also provided at a forward position on the outer circumference of the housing 130.

Further, as shown in FIGS. 2, 4 and 6, a part of the housing 130 on a more distal end side than the diameter-increased part 130f projects more forward than the distal end face 121s in a state that the fitted part 130e is fitted in the mounting hole 121ha, and the acoustic lens 39 is exposed in a circumferential manner when the balloon 199 is removed.

Note that the ultrasound transducer 35 described above is provided in the distal end side part of the housing 130, and a drawing-out hole 130eh for drawing out an ultrasound transducer cable 40 extending from the ultrasound transducer 35 backward, which passes through the fitted part 130e along the insertion direction S, is formed in the fitted part 130e.

Further, as shown in FIGS. 4 to 6, and FIG. 8, a screw receiving member 130b is fitted at a position more forward than the O-shaped ring 65 on an outer circumference of the fitted part 130e. Note that the screw receiving member 130b may be formed integrally with the housing 130.

As shown in FIGS. 5 and 8, two V-shaped grooves 130u communicating with the respective female screw portions 121n in the diameter direction K are formed on the screw receiving member 130b. Note that the number of the V-shaped grooves 130u is not limited to two and is required only to be a same number as the female screw portions 121n.

As shown in FIG. 8, the sharp tips of the fully threaded screws 80 screwed into the female screw portions 121n are in contact with the V-shaped grooves 130u.

Accordingly, when the fully threaded screws 80 are fastened relative to the female screw portions 121n, the fitted part 130e of the housing 130 moves backward by a component force of rear-side slopes 81t of the sharp tips of the fully threaded screws 80 pressing the V-shaped grooves 130u to an inner side in the diameter direction K.

After that, a proximal end 130et of the fitted part 130e is pressed against an abutting face 121i of the distal end portion body 121, which is formed at a midway position of the mounting hole 121ha in the insertion direction S, backward.

As a result, the housing 130 is positioned in the insertion direction S and fixed to the mounting hole 121ha, and the housing 130 is difficult to come off forward.

Further, since the fitted part 130e is positioned and fixed in the mounting hole 121ha by the proximal end 130et being pressed to the abutting face 121i, a circumferential gap D has occurred due to design tolerance as described above between the diameter-increased part 130f and the distal end face 121s of the distal end portion body 121 in the insertion direction S as shown in FIGS. 4 and 6.

Note that, in the present embodiment also, the circumferential gap D is filled with adhesive not shown so that dirt does not accumulate.

Further, as shown in FIGS. 3 and 6, at a position on a more distal end side than the V-shaped grooves 130$u$ on an outer circumference of the screw receiving member 130$b$, a projecting portion 130$t$ which projects outside in the diameter direction K and which is to be fitted into the fitting groove 121$m$ formed on the distal end face 121$s$ when the fitted part 130$e$ is fitted into the mounting hole 121$ha$ and fixed is formed.

Note that, as for the projecting portion 130$t$, a plurality of projecting portions 130$t$, for example, a same number as the number of the fitting grooves 121$m$ may be provided.

Further, when being fitted into the fitting groove 121$m$, the projecting portion 130$t$ is positioned near the distal end opening of each balloon conduit 19 in the circumferential direction R similarly to the fitting groove 121$m$.

Note that, as shown in FIG. 3, the projecting portion 130$t$ may be provided with visual confirmation means M configured to cause an operator to visually confirm the projecting portion 130$t$. As examples of the visual confirmation means M, color, a character, a symbol and the like are given.

The reason is as follows. Usually, when the balloon 199 is used for the ultrasound transducer unit 30, liquid is supplied to the balloon 199 fixed to the ultrasound transducer unit 30 via the fluid supply conduit between the balloon conduits 19 to cause the balloon to swell. However, air in the fluid supply conduit between the balloon conduits 19 is also supplied to the balloon 199 accompanying supply of the liquid. Therefore, the operator collects air in the balloon 199 to a vicinity of the distal end opening of the fluid suction conduit between the balloon conduits 19 by manual work such as kneading the balloon 199 from outside to perform work of sucking air. At this time, if the visual confirmation means is provided on the projecting portion 130$t$ positioned near each balloon conduit 19 in the circumferential direction R, the operator can easily recognize a position of the distal end opening of the fluid suction conduit between the balloon conduits 19 from a position of the projecting portion 130$t$ and, therefore, can easily perform the work of removing air from the balloon 199.

Furthermore, the operator can visually confirm a boundary between the fitting groove 121$m$ and the projecting portion 130$t$ easily and easily recognize a position where a tool such as a screwdriver is to be inserted. Therefore, the visual confirmation means M may be provided in the fitting groove 121$m$.

Further, by the projecting portion 130$t$ being fitted in the fitting groove 121$m$, the housing 130 is prevented from rotating in the circumferential direction R relative to the distal end portion body 121.

That is, by the projecting portion 130$t$ being fitted in the fitting groove 121$m$, the housing 130 is positioned in the circumferential direction R relative to the distal end portion body 121.

Here, in the state that the projecting portion 130$t$ is fitted in the fitting groove 121$m$, a gap C of about several millimeters for removal of the ultrasound transducer unit 30 is formed between the projecting portion 130$t$ on the distal end face 121$s$ and the fitting groove 121$m$, specifically, between an outer circumferential face of the projecting portion 130$t$ and an inner circumferential face of the fitting groove 121$m$ in the diameter direction K as shown in FIGS. 3 and 6.

The gap C is exposed forward, for example, as shown in FIG. 3 at a position where the operator can visually recognize the gap C.

Note that the gap C may be exposed, facing a direction other than the forward direction in the insertion direction S, depending on the position where the fitting groove 121$m$ is formed on the distal end portion body 121, as far as the gap C is positioned at a position where the operator can visually confirm the gap C.

Further, the gap C is not required to be always exposed and may be covered with a cover or the like. The gap C may be exposed by removing the cover or the like when the ultrasound transducer unit 30 is removed.

The gap C constitutes space where a tool such as a screwdriver is inserted when the housing 130 is removed from the distal end portion body 121.

Next, operation of the present embodiment will be briefly described.

First, at the time of removing the ultrasound transducer unit 30 from the distal end portion 21, specifically, at the time of removing the housing 130 from the distal end portion body 121, the operator removes the fully threaded screws 80 from the female screw portions 121$n$ after removing the balloon 199 from the ultrasound transducer unit 30.

After that, a distal end side of a tool such as a screwdriver is inserted into the gap C exposed forward on the distal end face 121$s$, from forward in the insertion direction S. A distal end of the tool is inserted into a contact face 130$bt$ side of the projecting portion 130$t$, which is in contact with a face of the fitting groove 121$m$ exposed forward in the insertion direction S. After that, by inclining the tool in the projecting portion 130$t$, the housing 130 is pulled off forward from the distal end portion body 121 by utilizing a principle of leverage.

At this time, if a step portion 130$bd$ is formed on a part of the contact face 130$bt$ of the projecting portion 130$t$ as shown in FIG. 7, a space is generated by the step portion 130$bd$ rearward of the contact face 130$bt$, and, therefore, the distal end of the tool easily enters the contact face 130$bt$ side. Thus, it becomes easy to pull off the housing 130.

Further, though the gap D described above is filled with adhesive in the present embodiment also as described above, the adhesive in the gap D is broken at the time of performing the work of inserting a tool in the gap C and pulling off the housing 130 forward. Therefore, it becomes unnecessary to perform work of removing the adhesive in the gap D using a knife or the like as done conventionally.

Thus, in the present embodiment, it has been shown that, when the fitted part 130$e$ of the housing 130 is fitted and fixed in the mounting hole 121$ha$ of the distal end portion body 121, the projecting portion 130$t$ of the housing 130 is fitted into the fitting groove 121$m$ formed on the distal end face 121$s$ of the distal end portion body 121, and, thereby, the gap C for removal of the ultrasound transducer unit 30 occurs between the projecting portion 130$t$ and the fitting groove 121$m$.

According to the above, at the time of removing the ultrasound transducer unit 30 from the distal end portion 21, the operator inserts a distal end side of a tool into the gap C exposed forward from forward after removing the balloon 199 and removing the fully threaded screws 80 from the female screw portions 121$n$, inserts the distal end of the tool into the contact face 130$bt$ side after that, and inclines the tool. Thereby the operator can easily pull of the housing 130 from the distal end portion body 121 forward while breaking adhesive filled in the gap D utilizing the principle of leverage.

Therefore, since it is not necessary to grasp the housing 130 with the operator's fingers or the tool at the time of pulling off the housing 130 forward, it does not happen that the acoustic lens 39 is scratched by the fingers or the tool.

Further, since it is not necessary to remove adhesive filled in the gap D with a knife or the like inserted into the adhesive from outside in the diameter direction K, it does not happen that the acoustic lens 39 is scratched by the knife or the like.

Therefore, it is possible to provide the ultrasound endoscope 1 which is provided with a configuration in which the ultrasound transducer unit 30 can be easily removed from the distal end portion 21 of the insertion portion 2.

Furthermore, in the present embodiment, it has been shown that the fully threaded screws 80 are used to fix the housing 130 to the distal end portion body 121.

According to the above, since it is not necessary to use countersunk screws having head portions, it is not necessary to form counterbore holes as conventionally done to prevent head portions of screws to protrude outside in the diameter direction K, in the distal end portion body 121.

According to the above, it is possible to shorten a length of the distal end portion body 121 in the insertion direction S by a length of the counterbore holes, that is, a length of the head portions of the countersunk screws, and it is possible to improve operability of the insertion portion 2.

Note that, in the embodiment described above, the time of removing the housing 130 from the distal end portion body 121 has been described as an example. Regardless of this, the configuration in which the gap between the projecting portion and the fitting groove is utilized for removal may be, of course, applied to removal between other frame bodies. For example, the configuration is applicable to removal of a frame body constituting the image pickup unit 70 from the mounting hole 121hb of the distal end portion body 121.

What is claimed is:

1. An ultrasound endoscope comprising:
   an insertion portion configured to be inserted into a subject,
      wherein the insertion portion comprises a distal end portion provided at a distal end of the insertion portion, and
      wherein the distal end portion comprises a fitting groove; and
   an ultrasound transducer comprising a projecting portion projecting outwardly in a radial direction of a longitudinal axis of the insertion portion,
      wherein the projecting portion is configured to be freely fitted into the fitting groove, and
      wherein in an arrangement where the projecting portion is fitted into the fitting groove:
         a circumferential gap is formed between a distal end face of the distal end portion and a diameter-increased part of the ultrasound transducer, wherein the ultrasound endoscope further comprises an adhesive filled into the circumferential gap; and
         a tool-receiving gap is formed between the projecting portion and the fitting groove, wherein the tool-receiving gap is configured to receive a tool, and wherein the tool-receiving gap is arranged relative to the circumferential gap such that when the tool is received in the tool-receiving gap and the tool is inclined, a force exerted by the inclined tool breaks the adhesive in the circumferential gap and pulls the ultrasound transducer off from the distal end portion of the insertion portion.

2. The ultrasound endoscope according to claim 1, wherein the tool-receiving gap is exposed forward in an insertion direction of the insertion portion.

3. The ultrasound endoscope according to claim 1, wherein the projecting portion has a step portion on a part of a face to be in contact with the fitting groove.

4. The ultrasound endoscope according to claim 1, wherein the projecting portion is provided with a marker configured to enable the projecting portion to be visually confirmed.

5. The ultrasound endoscope according to claim 1, wherein the distal end portion comprises a distal end portion body having the fitting groove formed on the distal end face of the distal end portion,
   wherein the distal end face of the distal end portion defines an ultrasound transducer mounting hole formed inside, and
   wherein the ultrasound transducer comprises:
      the projection portion on an outer circumference; and
      a housing, wherein a part of the housing is configured to be fitted into the ultrasound transducer mounting hole,
   wherein at least one female screw portion into which at least one screw is screwed is formed on the distal end portion body, and
   wherein at least one V-shaped groove configured so that the tip of the at least one screw screwed into the at least one female screw portion is abutted against the at least one V-shaped groove is formed on a fitted part of the housing configured to be fitted to the distal end portion body.

6. The ultrasound endoscope according to claim 5, wherein the screw is a fully threaded screw.

7. An ultrasound endoscope comprising:
   an insertion portion configured to be inserted into a subject,
      wherein the insertion portion comprises a distal end portion provided at a distal end of the insertion portion, and
      wherein the distal end portion comprises at least one fitting groove;
   an ultrasound transducer comprising at least one projecting portion, wherein each of the at least one projecting portion projects outwardly in a radial direction of a longitudinal axis of the insertion portion; and
   a fixing member configured to fix the distal end portion and the ultrasound transducer to each other in an arrangement where the each of the at least one projecting portion is fitted into a corresponding one of the at least one fitting groove such that:
      a circumferential gap is formed between a distal end face of the distal end portion and a diameter-increased part of the ultrasound transducer, wherein the ultrasound endoscope further comprises an adhesive filled into the circumferential gap; and
      a tool-receiving gap is formed between the each of the at least one projecting portion and the corresponding one of the at least one fitting groove, wherein the tool-receiving gap is configured to receive a tool, and wherein the tool-receiving gap is arranged relative to the circumferential gap such that when the tool is received in the tool-receiving gap and the tool is inclined, a force exerted by the inclined tool breaks the adhesive in the circumferential gap and pulls the ultrasound transducer off from the distal end portion of the insertion portion.

8. The ultrasound endoscope according to claim 7, wherein the fixing member comprises a screw.

* * * * *